United States Patent
Dehn et al.

(10) Patent No.: US 9,758,504 B2
(45) Date of Patent: Sep. 12, 2017

(54) METHOD FOR PRODUCING 2,3,5-TRIMETHYL BENZOQUINONE BY OXIDATION OF 2,3,6-TRIMETHYLPHENOL

(71) Applicant: BASF SE, Ludwigshafen (DE)

(72) Inventors: Richard Dehn, Ludwigshafen (DE); Michael Kraus, Frankenthal (DE); Martine Dehn, Ludwigshafen (DE); Manuel Danz, Plankstadt (DE); Joaquim Henrique Teles, Waldsee (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/902,231

(22) PCT Filed: Jun. 25, 2014

(86) PCT No.: PCT/EP2014/063425
§ 371 (c)(1),
(2) Date: Dec. 30, 2015

(87) PCT Pub. No.: WO2015/000767
PCT Pub. Date: Jan. 8, 2015

(65) Prior Publication Data
US 2016/0368887 A1    Dec. 22, 2016

Related U.S. Application Data

(60) Provisional application No. 61/841,946, filed on Jul. 2, 2013.

(30) Foreign Application Priority Data

Jul. 2, 2013  (EP) .................................. 13174688

(51) Int. Cl.
*C07C 45/00* (2006.01)
*C07D 311/72* (2006.01)
*C07C 46/08* (2006.01)
*C07C 50/02* (2006.01)
*C07C 50/04* (2006.01)

(52) U.S. Cl.
CPC ............ *C07D 311/72* (2013.01); *C07C 46/08* (2013.01); *C07C 50/02* (2013.01); *C07C 50/04* (2013.01)

(58) Field of Classification Search
CPC ........ C07D 311/72; C07C 50/04; C07C 46/08
USPC ......................................................... 568/309
See application file for complete search history.

(56) References Cited

U.S. PATENT DOCUMENTS

| | | |
|---|---|---|
| 3,796,732 A | 3/1974 | Brenner |
| 6,262,311 B1 | 7/2001 | Maassen et al. |

FOREIGN PATENT DOCUMENTS

| | | |
|---|---|---|
| DE | 2 221 624 A1 | 11/1972 |
| DE | 2 139 692 A1 | 2/1973 |
| EP | 127 888 A1 | 12/1984 |
| EP | 167 153 A1 | 1/1986 |
| EP | 0 216 351 A2 | 4/1987 |
| EP | 294 584 A1 | 12/1988 |
| EP | 0369823 A1 | 5/1990 |
| EP | 0475272 A2 | 3/1992 |
| EP | 1 092 701 A1 | 4/2001 |
| JP | 55072136 | 5/1980 |

OTHER PUBLICATIONS

International Search Report for PCT/EP2014/063425 mailed Jul. 23, 2014.
Written Opinion for PCT/EP2014/063425 mailed Jan. 8, 2015.
European Office Action for European Application No. 16187815.2 dated Jan. 18, 2017.

*Primary Examiner* — T. Victor Oh
(74) *Attorney, Agent, or Firm* — Drinker Biddle & Reath LLP

(57) ABSTRACT

The invention relates to a method for producing 2,3,5-trimethyl benzoquinone or a compound containing 2,3,5-trimethyl benzoquinone, the method comprising the following steps: Oxidation of 2,3,6-trimethylphenol with oxygen or an oxygen-containing gas in a two- or multi-phase reaction medium in the presence of a catalyst or catalyst system containing at least one copper (II)-halide to a mixture containing 2,3,5-trimethyl benzoquinone, characterized in that the reaction medium contains water and at least one secondary aliphatic acyclic alcohol having 6 or more, preferably 7 or more, carbon atoms.

12 Claims, No Drawings

METHOD FOR PRODUCING 2,3,5-TRIMETHYL BENZOQUINONE BY OXIDATION OF 2,3,6-TRIMETHYLPHENOL

CROSS-REFERENCE TO RELATED APPLICATIONS

This application is a national stage application (under 35 U.S.C. §371) of PCT/EP2014/063425, filed Jun. 25, 2014, which claims benefit of European Application No. 13174688.5, filed Jul. 2, 2013, and U.S. Application No. 61/841,946, filed Jul. 2, 2013, all of which are incorporated herein by reference in their entirety.

The present invention provides a process for preparing 2,3,5-trimethylbenzoquinone or a mixture comprising 2,3,5-trimethylbenzoquinone, comprising the following step: oxidizing 2,3,6-trimethylphenol with oxygen or an oxygen-containing gas in a two-phase or multiphase reaction medium in the presence of a catalyst or catalyst system at least comprising a copper(II) halide to give a mixture comprising 2,3,5-trimethylbenzoquinone, wherein the reaction medium comprises water and at least one secondary aliphatic acyclic alcohol having 6 or more, preferably 7 or more, carbon atoms.

A further aspect of the present invention relates to a mixture comprising 2,3,5-trimethylbenzoquinone, the mixture being preparable or prepared by the process of the invention.

The present invention additionally provides the use of a secondary aliphatic acyclic alcohol having 6 or more, preferably 7 or more, carbon atoms as solvent in the oxidation of 2,3,6-trimethylphenol to 2,3,5-trimethylbenzoquinone.

Furthermore, the present invention relates to the use of the 2,3,5-trimethylbenzoquinone prepared by the process of the invention, or of a mixture comprising 2,3,5-trimethylbenzoquinone and prepared by the process of the invention, in the synthesis of vitamin E, more particularly for the preparation of 2,3,6-trimethylhydroquinone.

2,3,6-Trimethylbenzoquinone (1) is of great importance as a precursor for the industrial synthesis of cetocopherol, i.e., vitamin E (3). For this synthesis, (1) is first catalytically hydrogenated to 2,3,6-trimethylhydroquinone (2), and then subjected to condensation with Isophytol, using a Lewis acid as catalyst, to form (3) (scheme 1).

Scheme 1: Industrial synthesis of α-tocopherol (3).

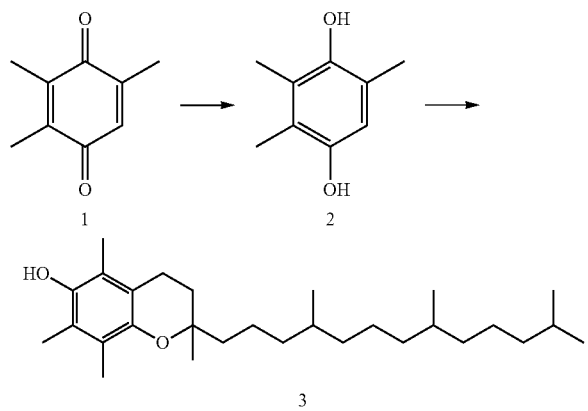

There are a series of industrially realized syntheses known for the synthesis of (1). Almost all of the processes known from the prior art synthesize (1) using the oxidation of 2,3,6-trimethylphenol (4), which in turn can be obtained by a variety of routes. For the oxidation of (4) to (1), oxygen is used preferably, as an inexpensive oxidizing agent (scheme 2).

Scheme 2: Synthesis of 2,3,6-trimethylbenzoquinone (1).

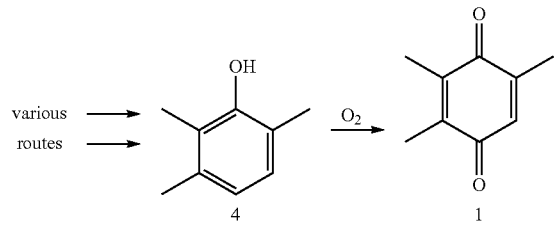

The most efficient processes for the oxidation of (4) to (1) use copper(II) halides or copper(II)-halogen complexes as catalysts. These processes, however, are not without their attendant problems. Instances include, for example, the costly and inconvenient recycling of the solvent used and/or of the catalyst used, and, in particular, the formation of unwanted byproducts. Particularly noteworthy is the formation of halogenated, generally chlorinated, byproducts, which break down during workup, releasing HCl, and so lead to corrosion and to losses of the product (1) of value.

DE 2 221 624 describes the oxidation of 2,3,6-trimethylphenol with oxygen in the presence of copper halides, primarily copper(II) chloride dihydrate, in polar solvents which are water-soluble or of unlimited miscibility with water—preferably dimethylformamide. A disadvantage of this process, however, is that it is difficult to isolate the product from the reaction mixture and to return the catalyst.

EP 127 888 describes the use of copper(II)-halide complexes having the general formula $M_q[Cu(II)_mX_n]_p$, such as $Li[CuCl_3]$ or $K_2[CuCl_4]$, for example, as catalysts for the oxidation of 2,3,6-trimethylphenol with oxygen in a mixture of water and an aliphatic alcohol having 4 to 10 carbon atoms as solvent. Because the solvent exhibits a miscibility gap with water, the reaction takes place in a mixture composed of two liquid phases. As a result, high reaction rates are achieved, and the catalyst is easy to return, as an aqueous solution, by means of a phase separation. The aliphatic alcohols used may comprise 4 to 10 carbon atoms, preferably 5 to 10 carbon atoms. Preferred solvents stated are primary alcohols, examples being n-butanol, n-amyl alcohol, isoamyl alcohol, n-hexanol, 2-ethylhexanol, n-heptanol, n-octanol, n-nonanol, and n-decanol.

EP 167 153 describes the use of the same catalyst as in EP 127 888 in a mixture of water and aliphatic alcohols having 5 to 10 carbon atoms as solvents. Stated with preference are primary alcohols, as for example n-amyl alcohol, isoamyl alcohol, n-hexanol, 2-ethylhexanol, n-heptanol, n-octanol, n-nonanol, and n-decanol. The reaction is carried out in "semibatch" mode, meaning that fewer byproducts are formed. The reaction, furthermore, is easier to control, and less catalyst is required.

EP 294 584 describes the use of a mixture of copper(II) chloride and lithium chloride as catalyst, and, as solvent, an aqueous mixture of an aromatic hydrocarbon and an aliphatic alcohol having 1 to 4 carbon atoms. Stated by way of example are the primary alcohols methanol, ethanol, n-propanol, isopropanol, n-butanol, 2-butanol, and tert-butanol. A number of secondary and tertiary alcohols are in fact stated, but only in combination with an aromatic hydrocarbon. Furthermore, these alcohols have a maximum of 4 carbon atoms. The comparison of examples 9 and 11 of EP 294 584, moreover, shows that the use of isopropanol as secondary alcohol leads to lower yields than the use of n-propanol (91.6 against 94.1%, under otherwise identical conditions). Furthermore, the use of a solvent mixture results in a significantly complicated solvent recycling procedure.

EP 369 823 describes the use of copper (II) chloride in combination with certain nitrogen compounds (hydroxylammonium salts, oximes, or ammonium salts) as catalyst. Solvents used are preferably aliphatic alcohols having 3 to 10 carbon atoms, those used with particular preference being branched alcohols having 3 to 6 carbon atoms and, with very particular preference, tertiary alcohols, such as tert-butanol or tert-amyl alcohol. However, the best yields of (1) that are achieved here (example 55: 94.5% with tert-amyl alcohol and 95% with tert-butanol) are situated at best at the same level as described in earlier specifications in the prior art that do not require the addition of nitrogen compounds.

M. Shimizu et al. (*Bull. Chem. Soc. Jpn.* 65 (1992) 1522) disclose a process for oxidizing (4) using mixtures of Cu(II) chloride and hydrochlorides of various amines, hydroxylamine, or oximes as catalyst system. Here again, solvents used include not only primary alcohols but also secondary alcohols, such as isopropanol, sec-butanol, 2-pentanol and 3-pentanol, tert-butanol, and tert-amyl alcohol, without any particular advantage becoming evident for the use of secondary alcohols. The preferential use of hydroxylamine as an adjuvant, which is consumed in the oxidation, makes this process unattractive.

EP 475 272 describes the use of mixtures of copper(II) chloride and alkaline earth metal chlorides, especially $MgCl_2$, as catalyst. Solvents listed are saturated aliphatic alcohols having 5 to 10 carbon atoms. Stated as particularly preferred are 1-pentanol, 1-hexanol, 1-heptanol, 1-octanol, 1-nonanol, 1-decanol, 2-ethyl-1-hexanol, and cyclohexanol—in other words, apart from cyclohexanol, primary alcohols.

EP 1 092 701 describes the use of mixtures of copper(II) chloride and other metal chlorides from the group of Fe, Cr, Mn, Co, Ni, Zn, or rare earths as catalysts. Solvents listed are branched and unbranched aliphatic alcohols having 5 to 10 carbon atoms. Stated as particularly preferred are 1-pentanol, 1-hexanol, 1-heptanol, 1-octanol, 1-nonanol, 1-decanol, 2-ethyl-1-hexanol, and cyclohexanol—in other words, apart from cyclohexanol, primary alcohols.

JP 55 072 136 describes the use of copper(II) chloride dihydrate as a catalyst in polyethylene glycols, such as $CH_3O(CH_2CH_2O)_9CH_3$, for example, as solvent. The reaction mixture can be worked up aqueously in order to return the catalyst. The desired product is removed by distillation as a low boiler. A disadvantage of this process, however, is that high-boiling byproducts become concentrated in the solvent and are difficult to remove.

Like all processes based on Cu halide catalysts, then, the processes described above also have fundamental disadvantages originating from the formation of organochlorine byproducts. These byproducts come about during the implementation of the oxidation reaction, and result from the chlorination of the reactant (4), of the product (1), and optionally of the 1-hexanol solvent. Below shows a number of typical byproducts, but without giving a complete listing.

Figure 1: Typical byproducts in the oxidation of 2,3,6-trimethylphenol (4) to 2,3,6-trimethylbenzoquinone (1).

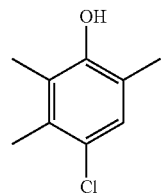

7

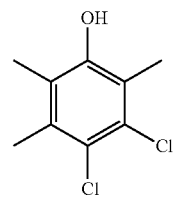

8

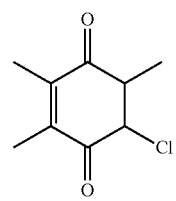

9

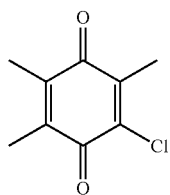

10

11

$C_6H_{12}ClOH$

The chlorination reactions which occur have the effect of a direct loss of selectivity in the desired oxidation reaction, and also, possibly, a loss of solvent, which must be compensated by addition of fresh solvent. At the same time, the catalyst phase is depleted of chloride, and for this reason the catalyst phase has to be treated with hydrochloric acid at regular intervals for the purpose of regeneration.

Furthermore, particularly under thermal load, the organochlorine byproducts give off hydrogen chloride, leading to significant corrosion problems in the corresponding plant parts (e.g., in distillation columns in which the reaction mixture is heated), meaning that expensive specialty steels have to be used for virtually all areas of the plant. Furthermore, hydrogen chloride induces decomposition reactions of the product (1) of value, leading to losses of yield, particularly in the liquid phase of the distillation column. The organochlorine byproducts (e.g., the compounds (7)-(11) shown in FIG. 1) generally having boiling points which are similar to that of the solvent or to that of the product, thereby hindering the distillative separation of the reaction mixture and giving rise to both product loss and solvent loss in middle-boiler fractions. Chlorinated impurities also poison the hydrogenation catalyst in the subsequent reaction of the quinone (1) to give the hydroquinone (2).

In order to avoid these disadvantages, additional workup steps are generally carried out. EP 0 216 351 discloses a concept for the removal of organochlorine byproducts from crude discharges from the $CuCl_2$ mediated oxidation of (4) to (1). Depletion of the byproducts is accomplished here by base scrubbing. Base scrubbing, however, is not particularly effective, and always implies a compromise between reduction in organochlorine compounds and losses of product. Overall, this measure does permit technical realization of the process according to scheme 3, but the additional process step represented by the base scrub results in higher capital costs and production costs, in losses of yield, and therefore, all in all, only to an alleviation of the problem described here.

A primary object of the present invention, accordingly, is to provide a process for preparing 2,3,5-trimethylbenzoquinone or a mixture comprising 2,3,5-trimethylbenzoquinone by oxidation of 2,3,6-trimethylphenol in the presence of a catalyst or catalyst system at least comprising a copper(II) halide, said process having all of the advantages of the processes known from the prior art, but minimizing the formation of the unwanted chlorinated byproducts.

A preferred object of the present invention is the provision of a process for preparing 2,3,5-trimethylbenzoquinone or a mixture comprising 2,3,5-trimethylbenzoquinone by oxidation of 2,3,6-trimethylphenol in the presence of a catalyst or catalyst system at least comprising a copper(II) halide that very largely avoids the formation of chlorinated byproducts, in order thereby to improve the selectivity of the reaction, to minimize the solvent loss through chlorination of the solvent, and optionally to avoid the need for additional workup steps and for the use of specialty materials.

It has now surprisingly been found that through the use of a secondary aliphatic acyclic alcohol having 6 or more, preferably 7 or more, carbon atoms as solvent in the oxidation of 2,3,6-trimethylphenol in the presence of a catalyst or catalyst system at least comprising a copper(II) halide, it is possible greatly to suppress the formation of chlorinated byproducts, while at the same time retaining all of the advantages known from the prior art.

The present invention therefore provides a process for preparing 2,3,5-trimethylbenzoquinone or a mixture comprising 2,3,5-trimethylbenzoquinone, comprising the following step: oxidizing 2,3,6-trimethylphenol with oxygen or an oxygen-containing gas in a two-phase or multiphase reaction medium in the presence of a catalyst or catalyst system at least comprising a copper(II) halide to give a mixture comprising 2,3,5-trimethylbenzoquinone, wherein the reaction medium comprises water and at least one secondary aliphatic acyclic alcohol having 6 or more, preferably 7 or more, carbon atoms.

With the process of the invention, there is no need to use specialty steels or to have a base scrub. During the pure effective distillation, the crude product is much more stable under thermal load, thereby minimizing losses in yield and at the same time producing a purer and hence more high-value product.

Suitable in principle for the process of the invention are all aliphatic acyclic alcohols which comprise 6 or more, preferably 7 or more, carbon atoms. Particularly preferred is the use of 3-heptanol.

In one advantageous refinement of the process of the invention, the oxidation of 2,3,6-trimethylphenol (4) is carried out with an oxygen-containing nitrogen gas in a two-phase reaction medium in the presence of substoichiometric amounts of a CuCl₂ catalyst and stoichiometric amounts of LiCl (scheme 3).

Scheme 3: Advantageous refinement of the process of the invention.

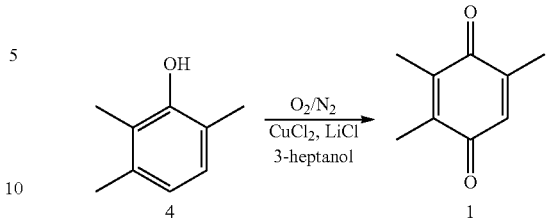

Of the process of the invention, the formation of organochlorine byproducts in the oxidation reaction of 2,3,6-trimethylphenol (4) to 2,3,5-trimethylbenzoquinone (1) is greatly reduced.

As well as the significant reduction in the organochlorine byproducts, effluence from the oxidation reaction carried out in secondary alcohols are found to have greatly reduced amounts of metal ions and chloride ions, and much less water. This facilitates the extraction for the recovery of the catalyst in solution in the organic phase. Since the phase separation during aqueous workup is much quicker, the workup approach becomes shorter and easier, considerably, by comparison with the use of primary alcohols as solvents. Given the fact, moreover, that the water-solubility of secondary alcohols is lower than that of primary alcohols having the same number of carbons, there is also a reduction in the solvent loss during the extraction.

In the advantageous refinement, described above, of the process of the invention, the reaction mixture consists of a lower, aqueous catalyst phase and of an upper, organic phase which comprises solvent, substrate, and reaction products. An oxygen-nitrogen stream is fed into this two-phase mixture with stirring. The process preferably takes place batchwise.

In one advantageous refinement of the process of the invention, the mixture comprising 2,3,5-trimethylbenzoquinone is washed in a step (ii) with an aqueous alkaline solution.

It is preferred in accordance with the invention, furthermore, for the oxidation to be carried out at a temperature of between 50° C. and 65° C., preferably at a temperature of between 53 and 58° C.

It is further preferred in accordance with the invention for the oxidation to be carried out over a period of 4 to 8 hours, preferably over a period of 5-7 hours.

In one advantageous refinement of the process of the invention, the reaction medium, after oxidation has taken place, is subjected in a step (iii) to a phase separation, and the organic phase is extracted for recovery of the catalyst in solution in the organic phase.

The present invention also provides a mixture comprising 2,3,5-trimethylbenzoquinone, the mixture being preparable or prepared by the process of the invention.

Through the process of the invention it is possible to obtain a mixture comprising 2,3,5-trimethylbenzoquinone that has a chlorine content of less than 0.5 g/100 g and/or a lithium content of less than 0.3 g/100 g and/or a copper content of less than 240 mg/kg.

The present invention additionally provides the use of a secondary aliphatic acyclic alcohol having 6 or more, preferably 7 or more, carbon atoms as solvent in the oxidation of 2,3,6-trimethylphenol to 2,3,5-trimethylbenzoquinone.

Furthermore, the present invention relates to the use of the 2,3,5-trimethylbenzoquinone prepared by the process of the invention, or of a mixture comprising 2,3,5-trimethylbenzoquinone and prepared by the process of the invention, in the synthesis of vitamin E, more particularly for the preparation of 2,3,6-trimethylhydroquinone.

The invention is elucidated in more detail by the examples which follow.

Analysis:

At the end of the exemplary experiments, the phases were separated and separately weighed, and the organic phases were analyzed. Quantitative determination of the amount of (1) and (4) in the organic phases took place by gas chromatography. The total chlorine content was determined by elemental analysis, and the amount of chloride ions was determined by potentiometric titration with a silver nitrate solution. The difference between the two values gives the amount of organically bonded chlorine. The quantitative determination of copper and lithium took place by means of atomic emission spectroscopy (ICP-OES).

EXAMPLES 1 to 10

A 4 L steel reactor was charged with 657 g of an aqueous reaction medium consisting of 151 g of $CuCl_2 \cdot 2H_2O$, 150 g of LiCl, and 365 g of water, and with 818 g of the alcohol serving as solvent. With stirring, this two-phase mixture was brought to the desired starting temperature $T_D$, and an oxygen-containing gas mixture was passed through it under atmospheric pressure. When the temperature $T_D$ has been reached, a 60 wt % strength solution of 500 g of 2,3,5-trimethylphenol (4) in the alcohol serving as solvent is supplied at a constant rate over a period $t_D$. In order to complete the reaction, stirring is continued at the temperature $T_R$ for a time span $t_R$.

After the end of reaction and after cooling to room temperature, the phases are separated and weighed individually, and the organic phase is analyzed. The conversion of (4) is complete in all cases (>99.9%). There is little variation in the yield of quinone (1), which in all of the experiments is in the 90-95% range. The results are set out in table 1.

As shown by a comparison of the inventive examples (I 2, 4, 6, 8, 10) with the associated comparative examples (C 1, 3, 5, 7, 9), the amounts of organically bonded chlorine when the reaction is carried out in a secondary alcohol for inventive use are lower on average by a factor of 3.5 than when using a primary alcohol. The total chlorine content, copper content, and lithium content of the organic phase is likewise much lower (on average by a factor of 6 for total chlorine, by a factor of 4.5 for copper, and by a factor of 18 for lithium).

EXAMPLE 11

A reaction effluent obtained from example 17 (reaction in 3-heptanol) is first washed with water. When phase separation has taken place the organic phase is extracted by shaking with aqueous HCl (25 wt %) and than washed with water again. Sodium hydroxide solution (2 wt %) is added to bring the solution to a pH of 6, and the solvent is removed under reduced pressure to an extent such as to give an approximately 75 wt % strength solution of trimethylquinone (1).

In order to determine the thermal stability of this crude product, it is heated to 110° C. and the amount of (1) is determined at regular intervals by gas chromatography. After 125 hours, only 8% of the (1) originally present has undergone decomposition.

COMPARATIVE EXAMPLE 12

Example 11 was repeated with the effluent from example C1 (reaction in 1-hexanol as solvent). On heating to 110° C., 44% of the quinone (1) originally present had undergone decomposition after 125 hours.

The invention claimed is:

1. A process for preparing 2,3,5-trimethylbenzoquinone or a mixture comprising 2,3,5-trimethylbenzoquinone, comprising the following step:
   (i) oxidizing 2,3,6-trimethylphenol to 2,3,5-trimethylbenzoquinone with oxygen or an oxygen-containing gas in a two-phase or multiphase reaction medium in the presence of a catalyst or catalyst system at least comprising a copper(II) halide, to give a mixture comprising 2,3,5trimethylbenzoquinone,
   wherein the reaction medium comprises water and at least one secondary aliphatic acyclic alcohol having 6 or more carbon atoms.

2. The process according to claim 1, wherein said at least one secondary aliphatic acyclic alcohol having 7 or more carbon atoms.

3. The process according to claim 1, wherein the catalyst or the catalyst system comprises copper (II) chloride.

4. The process according to claim 1, wherein the catalyst or the catalyst system further comprises at least one alkali metal halide.

5. The process according to claim 4, wherein said at least one alkali metal halide is lithium chloride.

6. The process according to claim 1, wherein the reaction medium comprises 3-heptanol.

TABLE 1

Results of the oxidation experiments (I: inventive, C: comparative experiments).

| No. | Solvent | $t_D$, h | $T_D$, ° C. | $t_R$, h | $T_R$, ° C. | $O_2$, SL/h | $N_2$, SL/h | $Cl_{tot}$, g/100 g | $Cl^-$, g/100 g | $Cl_{organic}$, g/100 g | Cu, g/100 g | Li, mg/kg |
|---|---|---|---|---|---|---|---|---|---|---|---|---|
| C1 | 1-hexanol | 3.25 | 58 | 2.75 | 58 | 90 | 60 | 2.3 | 2.2 | 0.1 | 1.2 | 2100 |
| I2 | 3-heptanol | 3.25 | 58 | 2.75 | 58 | 90 | 60 | 0.31 | 0.27 | 0.04 | 0.22 | 70 |
| C3 | 1-hexanol | 2.00 | 53 | 4.00 | 65 | 90 | 60 | 2.5 | 2.3 | 0.2 | 1.1 | 2100 |
| I4 | 3-heptanol | 2.00 | 53 | 4.00 | 65 | 90 | 60 | 0.31 | 0.26 | 0.05 | 0.21 | 65 |
| C5 | 1-hexanol | 1.00 | 53 | 5.00 | 58 | 150 | 0 | 2.2 | 2.1 | 0.1 | 1.1 | 1800 |
| I6 | 3-heptanol | 1.00 | 53 | 5.00 | 58 | 150 | 0 | 0.29 | 0.28 | 0.01 | 0.21 | 60 |
| I7 | 3-heptanol | 1.00 | 53 | 5.00 | 1 h, 53° C. 4 h 58° C. | 150 | 0 | 0.34 | 0.27 | 0.07 | 0.21 | 70 |
| I8 | 2-octanol | 1.00 | 53 | 5.00 | 58 | 150 | 0 | 0.47 | 0.42 | 0.05 | 0.29 | 230 |
| C9 | 1-heptanol | 1.00 | 53 | 5.00 | 58 | 150 | 0 | 1.80 | 1.60 | 0.20 | 0.92 | 1500 |
| C10 | 1-octanol | 1.00 | 53 | 5.00 | 58 | 150 | 0 | 1.70 | 1.50 | 0.20 | 0.83 | 1300 |

7. The process according to claim 1, wherein the process is carried out batchwise.

8. The process according to claim 1, wherein the mixture comprising 2,3,5-trimethylbenzoquinone is washed in a step (ii) with an aqueous alkaline solution.

9. The process according to claim 1, wherein the oxidation is carried out at a temperature of between 50° C. and 65° C.

10. The process according to claim 1, wherein the oxidation is carried out at a temperature of between 53 and 58° C. and the oxidation is carried out over a period of 4 to 7 hours.

11. The process according to claim 1, wherein the oxidation is carried out over a period of 4 to 8 hours.

12. The process according to claim 1, wherein the reaction medium, after oxidation has taken place, is subjected in a step (iii) to a phase separation, and the organic phase is extracted for recovery of the catalyst in solution in the organic phase.

\* \* \* \* \*